(12) United States Patent
Saint Victor

(10) Patent No.: US 8,541,356 B2
(45) Date of Patent: *Sep. 24, 2013

(54) WATER-ACTIVATED "GREEN" MULTI-FUNCTIONAL WIPE

(75) Inventor: Marie-Esther Saint Victor, Glencoe, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 41 days.

This patent is subject to a terminal disclaimer.

(21) Appl. No.: 12/624,113

(22) Filed: Nov. 23, 2009

(65) Prior Publication Data

US 2010/0101605 A1    Apr. 29, 2010

(51) Int. Cl.
*C11D 17/00* (2006.01)

(52) U.S. Cl.
USPC .................. 510/438; 510/439; 15/104.93

(58) Field of Classification Search
None
See application file for complete search history.

(56) References Cited

U.S. PATENT DOCUMENTS

| | | | |
|---|---|---|---|
| 4,946,617 | A | 8/1990 | Sheridan et al. |
| 4,948,585 | A | 8/1990 | Schlein |
| 5,091,102 | A | 2/1992 | Sheridan |
| 5,094,770 | A | 3/1992 | Sheridan et al. |
| 5,919,471 | A | 7/1999 | Saferstein et al. |
| 6,269,513 | B1 | 8/2001 | Torobin |
| 6,730,621 | B2 | 5/2004 | Gott et al. |
| 6,734,157 | B2 | 5/2004 | Radwanski et al. |
| 6,846,480 | B2 | 1/2005 | Smith et al. |
| 7,132,377 | B2 | 11/2006 | Borgonjon et al. |
| 7,348,018 | B2 | 3/2008 | McAtee et al. |
| 7,608,573 | B1 | 10/2009 | Scheuing et al. |
| 7,618,931 | B1 | 11/2009 | Scheuing et al. |
| 2003/0022572 | A1 | 1/2003 | Gott et al. |
| 2005/0124519 | A1 | 6/2005 | Sherry et al. |
| 2005/0158369 | A1* | 7/2005 | Dorschner et al. ............ 424/443 |
| 2005/0164901 | A1 | 7/2005 | Foley et al. |
| 2005/0192201 | A1 | 9/2005 | Ford et al. |
| 2006/0128591 | A1* | 6/2006 | Albrecht et al. ............... 510/438 |
| 2006/0246120 | A1 | 11/2006 | Kelly et al. |
| 2007/0071537 | A1 | 3/2007 | Reddy et al. |
| 2008/0075748 | A1 | 3/2008 | Hasenoehrl et al. |
| 2008/0255023 | A1 | 10/2008 | Shimmin et al. |
| 2009/0165228 | A1 | 7/2009 | Kilkenny et al. |
| 2009/0202463 | A1 | 8/2009 | Pan et al. |
| 2010/0101605 | A1 | 4/2010 | Saint Victor |
| 2010/0136148 | A1 | 6/2010 | Saint Victor |
| 2010/0144584 | A1 | 6/2010 | Saint Victor |

FOREIGN PATENT DOCUMENTS

| | | |
|---|---|---|
| EP | 0412131 | 5/1990 |
| EP | 1 255 640 | 11/2002 |
| WO | WO 03/043480 | 5/2003 |
| WO | WO 2004/046301 | 6/2004 |
| WO | WO 2005/055797 | 6/2005 |
| WO | WO 2005/056745 | 6/2005 |
| WO | WO 2005/072594 | 8/2005 |
| WO | WO 2005/121303 | 12/2005 |
| WO | WO 2006/004572 | 1/2006 |
| WO | 2006071069 A1 | 7/2006 |
| WO | 2007070090 A1 | 6/2007 |

OTHER PUBLICATIONS

PCT/US2010/003037 International Search Report dated Mar. 10, 2011.

* cited by examiner

*Primary Examiner* — Necholus Ogden, Jr.

(57) ABSTRACT

Multi-functional wipes with desirable ecological profiles and improved performances are disclosed. The wipes may include a substrate and a cleaning composition, a disinfecting/sanitizing composition, and an optional fragrance composition releasably associated with the substrate. The compositions may be separated from one another and may be impregnated in or coated on distinct sections of the substrate. Unlike "wet" wipes preloaded with a dilute cleaning liquid, the disclosed wipes may be substantially dry and water-activated just prior to its application on a target surface.

17 Claims, No Drawings

WATER-ACTIVATED "GREEN" MULTI-FUNCTIONAL WIPE

BACKGROUND

1. Technical Field

An eco-friendly, or "green," multi-functional wipe that combines cleaning, disinfecting/sanitizing, and optional fragrance delivery is disclosed. The wipes may include a substrate and a cleaning composition, a disinfecting/sanitizing composition, and an optional fragrance composition releasably associated with the substrate. The compositions may be separated from one another and may be impregnated in or coated on distinct sections of the substrate. Unlike "wet" wipes preloaded with a dilute cleaning liquid, the disclosed wipes may be substantially dry and water-activated just prior to use on a target surface.

2. Description of the Related Art

Disposable cleaning wipes and pads are known in the art. The wipe generally incorporates a substrate and a cleaning composition into a single article to improve cleaning efficiency and convenience over conventional cleaning products in which the cleaning substrate and cleaning compositions are independently selected and applied to the surface to be cleaned. Thus, cleaning wipes have been widely used in car care, skin care, household cleaning, etc.

Known disposable cleaning wipes for cleaning hard-surfaces are typically wet and pre-loaded, i.e. impregnated with the cleaning composition without subsequent dilution before the wipes are applied to the target surface. Typically, those compositions include a substantial amount of water. For example, some cleaning compositions impregnated into conventional wipes may include from 50% to over 90% water. As a result of such high water contents, conventional wipes, especially those with substrates including natural or green fibers, tend to have a short shelf life due to the integrity of the fibers being weakened by the prolonged exposure to water.

Another effect of high water contents in conventional wipes is the increased weight, which may adversely affect transportation, handling, packaging and storage of the wipes. For example, some conventional wipes are preloaded with 6 to 7 grams of aqueous cleaning composition. More importantly, as the relatively dilute cleaning composition depletes, the effectiveness of conventional wipes may decrease rapidly. Therefore, only limited surface areas can be cleaned by a single wipe. For example, a single conventional wipe typically cannot clean an entire bathtub. Thus, regular household cleaning tasks, such as bathtub cleaning, would generally require quite a few conventional wipes, which not only increases the consumption of raw material used to manufacture the wipes but also requires more effort and energy to dispose and recycle the used wipes.

Finally, the high water content in conventional wipes generally necessitates the inclusion of preservatives, which not only increase the manufacturing cost of the wipe but also adversely affect the ecological profile of the wipes because the preservatives are generally synthetic and not derived from natural and renewable sources.

Multi-purpose household liquid products that function both as cleaners and disinfectants/sanitizers are also known in the art. However, cleaners with good cleaning performance sometimes have poor disinfecting/sanitizing properties, while disinfectants/sanitizers that demonstrate excellent disinfecting/sanitizing performance sometimes have poor cleaning properties. Moreover, products that combine good cleaning and disinfecting/sanitizing efficiencies typically include harsh chemicals, such as peroxygen bleach, hydrogen peroxide, glutaraldehyde and quaternary ammonium salts, which not only are toxic and/or incompatible to human skin but also have a less desirable ecological profile by including non-natural ingredients.

Natural and non-toxic disinfecting/sanitizing agents are known in the art. For example, naturally occurring essential oils and colloidal silver are both effective disinfecting/sanitizing agents with good antimicrobial activity. However, because essential oils and colloidal silver are generally immiscible with water, compositions based thereon typically include surfactants and/or solvents to disperse or solubilize the essential oils or colloidal silver. Nevertheless, the surfactants used in the compositions generally include petroleum-based surfactants which may lead to the formation of a less stable and less eco-friendly disinfectant composition.

Compositions for controlled release of active substances are also known in the art. For example, fragrance or insecticide compositions in the form of single-phase solution have been developed to allow prolonged release of a fragrance or insecticide into the air. However, those compositions generally have a less desirable ecological profile in order to maintain their fragrance or insecticide delivery performance.

In recent years, there has been a significant amount of global consumer awareness in green, i.e., eco-friendly, household or personal care products. As a result, increasing efforts have been directed to the development of household products with desirable ecological profiles. For example, products containing ingredients that are derived from natural and renewable sources, as well as products that are biodegradable in natural environments, have been a focus of this global "eco-friendly" trend.

Indeed, products derived from renewable resources, such as plants, contribute less greenhouse gas because of their closed $CO_2$ cycle. Specifically, during growth, plants consume the same amount of carbon dioxide ($CO_2$) and water ($H_2O$) as they subsequently release into the atmosphere by biodegradation after use. Therefore, products derived from renewable resources, such as plants, are considered to be "green" and having zero or reduced "carbon footprint" when compared with petrochemical-based products. Common ingredients in household products such as surfactants, fragrances, oils and solvents can be derived directly or indirectly from both renewable sources such as plant materials or non-renewable sources such as petroleum.

In particular, while most surfactants are still derived from petroleum chemicals, surfactants derived from plant-based carbohydrates and oils are becoming available. One suitable renewable raw material for surfactant production is glucose, which is reacted with alcohol to produce alkyl polyglycosides (also known as alkyl polyglucosides). Alkyl polyglycosides have been used in cosmetics products, agricultural formulations and as surfactants in industrial cleaning agents. Alkyl polyglycosides include a hydrophobic (or lipophilic) hydrocarbon chain is formed by a fatty alcohol (e.g., dodecanol, tetradecanol) obtained from a saturated tropical oils such as palm or coconut oil. The hydrophilic part of the molecule, derived from glucose or dextrose, maybe obtained from starch, brown algae, citrus or beet pulp, most commonly from corn.

In addition to its desirable ecological profile, alkyl polyglycosides have good compatibility with the eyes, skin and mucous membranes and even reduce the irritant effects of surfactant combinations. Alkyl polyglycosides are also completely biodegradable, both aerobically and anaerobically.

Some anionic surfactants may also have immediate precursors that are obtainable from natural and renewable sources. For example, long-chain alkyl sulfates may be conveniently prepared from fatty alcohols derived from coconut oils. In particular, sodium coco sulfate (SCS) is derived from pure coconut oil and includes a mixture of sodium alkyl sulfate with the main component being sodium lauryl sulfate. Sodium coco sulfate may be used in a wide variety of consumer products in which viscosity building and foam characteristics are of importance. It can be incorporated into shampoos, hand soaps, bath products, shaving creams and medicated ointments.

Thus, there is a need for a multi-functional wipe that combines cleaning, disinfecting/sanitizing, and optional fragrance delivery while avoiding compatibility problems among their ingredients. Moreover, there is a need for a multi-functional wipe that is substantially free of water for easier transportation, packaging, handling, and storage than conventional "wet" wipes that are pre-loaded with a diluted cleaning composition. Finally, there is a need for an eco-friendly multi-functional wipe with all ingredients derived from natural and renewable sources or having a higher percentage of ingredients that are derived from natural and renewable sources.

SUMMARY OF THE DISCLOSURE

In satisfaction of the aforementioned needs, multi-functional wipes with desirable ecological profiles and improved performances are disclosed. The wipes may include a substrate and a cleaning composition, a disinfecting/sanitizing composition, and an optional fragrance composition releasably associated with the substrate. The compositions may be separated from one another and may be impregnated in or coated on the substrate or distinct sections thereof. Unlike "wet" wipes preloaded with a dilute cleaning liquid, the disclosed wipes may be substantially dry and may be water-activated just prior to its application on a target surface.

As used in this disclosure, a "green" component or ingredient is defined as a substance that is obtainable from natural and renewable sources or is prepared from immediate precursor(s) obtainable from natural and renewable sources. The term "Natural Index" (NI) is used herein to refer to the weight percentage of the composition that includes ingredients that are either directly obtainable from natural and renewable sources or made from immediate precursors that are directly obtainable from natural and renewable sources.

In one embodiment, the substrate of the disclosed wipe may include green components such as natural fibers, naturally derived fibers, or a blend thereof. In a refinement, the substrate may be made entirely of green components. In another embodiment, the substrate may include synthetic fibers that are not derived from natural and renewable sources. The substrate of the disclosed wipe may be woven or nonwoven.

The disclosed wipe also includes a cleaning composition releasably associated with the substrate. In one embodiment, the cleaning composition is impregnated into a first section of the substrate. In another embodiment, the cleaning composition is coated onto the first section of the substrate.

The cleaning composition may have an improved ecological profile without sacrificing the cleaning performance thereof. To that end, the cleaning composition may include one or more "green" surfactants as cleaning agents. Moreover, the composition may further include other optional green ingredients such as green linkers (hydrophilic and/or lipophilic), green pH adjusting agents, green anti-streaking agent, etc.

In one embodiment, the cleaning composition is a cleaning composition that includes a green nonionic surfactant and water. In a refinement, the green nonionic surfactant may include an alkyl polyglycoside. In a further refinement, the cleaning composition may also include one or more green co-surfactants. The green co-surfactants may include an anionic surfactant such as sodium lauryl sulfate or sodium coco sulfate. The combination of green surfactants may synergistically improve cleaning performance of the composition.

In another embodiment, the cleaning composition includes one or more green surfactants, a green linker, and water. In a refinement, the one or more green surfactants may be nonionic, anionic, or a mixture of both. In another refinement, the green linker includes a hydrophilic linker, lipophilic linker, or a mixture of both. The combination of the green surfactant(s) and the green linker(s) may synergistically improve the cleaning performance of the composition. Moreover, when used as a glass cleaner, the cleaning composition may have less streaking than conventional glass cleaning products.

The disclosed wipe further includes a disinfecting/sanitizing composition releasably associated with the substrate. For example, the disinfecting/sanitizing composition may be impregnated in or coated on a second section of the substrate. The disinfecting/sanitizing composition may be separated from the cleaning composition to prevent any incompatibility among the various ingredients of the compositions. In one embodiment, the first and second sections of the substrate are distinct from each other.

The disinfecting/sanitizing composition may have an improved ecological profile without sacrificing its performance. To that end, the cleaning composition may include one or more "green" disinfecting/sanitizing agents, such as colloidal silver, organic acids, essential oils, and/or mixtures thereof.

The disclosed wipe may also optionally include a "green" fragrance composition releasably associated with the substrate. The fragrance composition may be impregnated in or coated on a third section of the substrate. The fragrance composition may be separated from the cleaning and disinfecting/sanitizing compositions to prevent any incompatibility among the various ingredients of the compositions. In one embodiment, the first, second, and third sections of the substrate are distinct from one another.

As disclosed herein, the compositions are "releasable associated" with the substrate in that the compositions remain associated with the substrate as long as the substrate remains substantially dry (e.g. during packing, transportation, and storage). In use, however, the disclosed wipe is activated by water (e.g. tap water) just prior to its application on a target surface, thereby releasing the cleaning, disinfecting/sanitizing, and fragrance compositions associated with the substrate, such as through the formation solutions, emulsions or suspensions of the compositions that are later transferred to the target surface when the wipe is applied thereon for cleaning, disinfecting/sanitizing and fragrance delivery benefits.

In one embodiment, a micro-emulsion of the cleaning composition is formed after water-activation to enable spontaneous solubilization of soil when the micro-emulsion is applied on the target surface. It is contemplated that the presence of the cleaning composition as micro-emulsions may also enhance disinfecting/sanitizing performance and/or fragrance delivery performance of the disclosed wipe.

Further, the use of tap water to activate the wipe just prior to use not only significantly reduces the weight of the wipe for more convenient packaging, storage, and transportation, but also reduces the consumption of distilled water used during the manufacturing of the conventional wet wipes, thereby further improving the ecological profile of the wipe.

The disclosed wipe may be suitable for a wide variety of cleaning tasks. For example, the wipe may be used as a glass-cleaning wipe, a bathroom-cleaning wipe, a floor cleaning wipe or even an all-purpose household cleaning wipe. In one embodiment, the wipe not only effectively removes soil from a target surface but also leave no visible residue on the target surface. In another embodiment, the wipe may reduce streak when used as a glass cleaner. Besides cleaning, the wipe may also provide disinfecting/sanitizing benefits to the target surface and may leave a long-lasting fresh scent on the surface for enhanced ambience.

Other advantages and features of the disclosed wipe and the method of use thereof to treat a target surface will be described in greater detail below. It will also be noted here and elsewhere that the disclosed wipe may be suitably modified to be used in a wide variety of household and other applications by one of ordinary skill in the art without undue experimentation.

DETAILED DESCRIPTION OF THE PRESENTLY PREFERRED EMBODIMENTS

This disclosure is generally related to an eco-friendly multi-functional wipe that combines cleaning, disinfecting/sanitizing and optional fragrance delivery. To evaluate the ecological profile a cleaning wipe or composition, the term Natural Index (NI) is used herein to refer to the weight percentage of the composition that includes ingredients that are either directly obtainable from natural and renewable sources or made from immediate precursors that are directly obtainable from natural and renewable sources.

For example, ingredients such as water, ethanol, lactic acid, citric acid, caustic soda, natural fragrances, natural fibers such as wood pulp and cotton, are all obtainable from natural and renewable sources. Moreover, compounds like alkyl polyglycosides, alkyl glucoside, sodium coco sulfate (sodium lauryl sulfate) used in the cleaning composition of the disclosed wipe may be made from immediate precursors (fatty alcohols, glucose, etc.) that are obtainable from natural and renewable sources. Similarly, naturally derived fibers used in the substrate of the disclosed wipe, such as rayon, lyocell, and viscose, may also be made from immediate precursors (wood pulp, cotton, etc.) that are obtainable from natural and renewable sources. Finally, the disinfecting/sanitizing agents used in the disclosed wipe, such as essential oils, colloidal silver, and organic acids may be obtainable from or made from immediate precursors that are obtainable from natural and renewable sources (botanic abstracts, silver, sugar etc.)

On the other hand, surfactants such as ethoxylated nonionic surfactants, alkylbenzene sulfonate anionic surfactants, and quaternary ammonium cationic surfactant are at least partially based on petroleum chemicals and thus do not contribute toward the NI of the composition. Similarly, truly synthetic fibers, such as nylon, polyester, acrylic, carbon fibers, glass fibers, metal fiber, etc., are also based on immediate precursors that are not obtainable from natural and renewable sources.

In a general embodiment, the disclosed wipe includes a substrate and a plurality of functional composition releasably associated with the substrate. The functional compositions may include a cleaning composition, a disinfecting/sanitizing composition, and an optional fragrance composition. As disclosed herein, the compositions or ingredients are "releasable associated" with the substrate in that the compositions or ingredients remain associated with the substrate as long as the substrate remains substantially dry (e.g. during packing, transportation, and storage). When the disclosed wipe is activated by water just prior to its application on a target surface, however, the cleaning, disinfecting/sanitizing, and fragrance compositions become dissociated from the substrate and are eventually transferred from the substrate to the treated surface.

The functional compositions may be separated from one another and may be impregnated in or coated on distinct sections of the substrate. In one embodiment, the substrate is loaded with from about 3% to about 5% of the functional compositions based on the weight of the substrate. Unlike "wet" wipes preloaded with a dilute cleaning liquid, the disclosed wipes may be substantially dry and water-activated just prior to its application on a target surface. As used in this disclosure, a wipe is "substantially dry" when the water content of the wipe less than 10 wt %. In some embodiments, the water content of the disclosed wipe may be less than 5 wt %, less than 2 wt % or even less than 1%. Moreover, the composition may be essentially free of organic solvents. Moreover, the composition may be VOC-free.

Substrate

The functional compositions (cleaning, disinfecting/sanitizing, fragrance) described above is releasably associated with a substrate and activated by water just prior to application on a target surface. To that end, one function of the substrate is that it provides a matrix in which the functional compositions can be not only retained during storage, handling and transportation but also diluted when the wipe is in contact with water just prior to use. Thereafter, the substrate may also functions as an applicator to deliver and distribute the diluted cleaning composition to the target surface. The functional compositions may be diluted multiple times before it is depleted from the substrate. Optionally, the substrate may also function to scrub the surface and to absorb at least some soil that is dislodged from the surface. Finally, the substrate is used as a vehicle to deliver the disinfecting/sanitizing agent and fragrance to the target surface.

The substrate of the disclosed wipe may include green fibers such as natural fibers, naturally derived fibers, or a blend thereof. The natural fibers may be cellulose-containing fibers including, but not limited to, cotton fiber, flax fiber, hemp fiber, sisal fiber, jute fiber, kenaf fiber, bamboo fiber, coconut fiber, and wood pulp. Naturally derived fiber suitable for use in this disclosure may include, but are not limited to, rayon, lyocell, and viscose or other materials derived from natural fibers. For example, lyocell may be derived from wood pulp, viscose may be derived from wood or cotton fibers, and rayon may be derived from a wide variety of cellulose-containing natural fibers.

In some non-limiting embodiments, the substrate may be made from a blend of natural and naturally derived fibers. For example, the substrate may include a blend of cotton and viscose fibers or a blend of wood pulp and viscose fiber. The substrate may include green fibers as a major component or may be made entirely of green fibers. In one embodiment, the substrate includes 50 wt % viscose or rayon and 50% cotton. In another embodiment, the substrate is a blend of 25 wt % viscose or rayon, 25 wt % lyocell, and 50% cotton. In yet another embodiment, the substrate is entirely made of viscose or entirely made of lyocell.

In some embodiments, the substrate may also include one or more synthetic fibers not derived from natural and renewable sources. Synthetic fibers suitable for use in the substrate of the disclosed wipe may include, but are not limited to, nylons, polyesters, acrylics, olefin fibers such as polyethylene and polypropylene, carbon fibers, glass fibers, metal fibers, etc. In one embodiment, the substrate may include a blend of polyester, viscose, and lyocell (Tencel®).

In some embodiments, the substrate may include synthetic fibers as a minor component of the substrate so that their inclusion does not substantially affect the ecological profile of the disclosed wipe. In other embodiments, however, the substrate may include synthetic fibers as a major component or may even be made entirely of synthetic fibers. The substrate may be woven or nonwoven.

Other factors that may affect the selection of a suitable substrate component include such considerations as integrity, hand feel, processability and cost. In general, the substrate should not excessively tear or fall apart during the application of the wipe on the target surface or the subsequent optional rewetting and reapplication processes.

The substrate may take one of a wide variety of physical forms. In one embodiment, the substrate is a woven or nonwoven sheet with suitable dimension for household cleaning tasks. Other forms for the substrate may include, but are not limited to fiber balls, beads or other forms of intercalation support structures. In one embodiment, the substrate has a uniform structure and free of any laminated configuration to facilitate even distribution or impregnation of the cleaning composition throughout the substrate. It is to be understood that the shape and dimension of the substrate would be apparent to those skilled in the art and should not be considered as limiting the scope of this disclosure.

Cleaning Composition

In a general embodiment, the cleaning composition of the disclosed wipe may include one or more green surfactants. The green nonionic surfactants of the cleaning composition may include, but are not limited to, sugar-based surfactants, polyol-based surfactants, alkyl ethers, and alkyl carbonates. The sugar-based surfactants may be alkyl polyglycoside (or alkyl polyglucoside) surfactants that are made from fatty alcohols in coconut oil and polyglucose in corn. In addition to its excellent ecological profile, alkyl polyglycosides are biodegradable, non-irritating to human skin, and effective in solubilizing fragrance oil in water.

The alkyl polyglycosides which can be used in the disclosed emotions correspond to the following Formula I:

$$R_1O(Z)_a \tag{I}$$

wherein $R_1$ is a monovalent organic radical having from about 4 to about 22 carbon atoms; Z is a saccharide residue having 5 or 6 carbon atoms; and a is a number having a value from 1 to about 6. For example, alkyl polyglycosides of formula I wherein Z is a glucose residue may be utilized. Such alkyl polyglycosides are commercially available, for example, as APG®, GLUCOPON®, or PLANTAREN® surfactants from Cognis, 5051 Estecreek Drive, Cincinnati, Ohio 45232.

Suitable alkyl ethers used as green surfactants in the cleaning composition may include ethers with $C_4$-$C_{22}$ alkyl chains on either side of the C—O—C bond ($R_1$—O—$R_2$). The alkyl chains ($R_1$, $R_2$) may be saturated or unsaturated. In one embodiment, the alkyl ether may be dicaprylyl ether.

Suitable alkyl carbonates used as green surfactants in the cleaning composition may include carbonates with $C_4$-$C_{22}$ alkyl chains on either side of the carbonate group

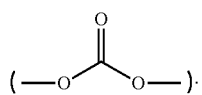

The alkyl chains may be saturated or unsaturated. In one embodiment, the alkyl ester may be dicaprylyl carbonate.

Other nonionic green surfactants suitable for use in the cleaning composition may include, but are not limited to, alkyl glucose amide, triglycerides, N-methyl coconut fatty acid glucamides (C12-14), amino acid-based surfactants, sugar esters, sorbital esters, sterol esters, glycolipid biosurfactants, etc.

In one embodiment, the cleaning composition may include from 5 to 80 wt %, more preferably from 5 to 75 wt % green nonionic surfactant(s). In another embodiment, the green nonionic surfactant(s) may be included at a level of from 8 to 65 wt %.

In addition to the green nonionic surfactant, the cleaning composition may optionally include one or more green co-surfactants. The green co-surfactants may be anionic, cationic, zwitterionic, or amphoteric surfactants prepared from immediate precursors that are obtainable from natural and renewable sources.

In one embodiment, the green anionic surfactants include one or more long-chain alkyl sulfates. Suitable alkyl sulfates includes, but are not limited to, sodium $C_8$-$C_{20}$ sulfates, ammonium $C_8$-$C_{20}$ sulfates, and mixtures thereof. In addition, the green anionic surfactant may also include surfactants based on alginates (cell-wall polyuronic acids from brown seaweeds) or ulvans (sulfated rhamnouronans from the cell wall of green seaweeds).

In a preferred embodiment, the green anionic surfactant includes sodium coco sulfate or sodium lauryl sulfate. Sodium coco sulfate may be prepared from sulfating coconut oil, which is made up of a wide range of fatty acids (ranging from as few as 8 carbon alkyl chains to as many as 20. The majority, e.g. 45-50%, of the fatty acids in coconut oil are fatty acids containing 12 carbons. Sodium lauryl sulfate, on the other hand, is a purified version of the sodium coco sulfate. During manufacturing of sodium lauryl sulfate, coconut oil is processed to remove most of the non-12 carbon fatty acids before the fatty acids are sulfated.

The green anionic surfactant may be used in the cleaning composition to synergistically improve the performance, such as soil removal, of the composition. Accordingly, a relatively low level of the green anionic surfactant is required. For example, the concentration of the green anionic surfactant(s) may range from about 5 to about 40 wt %, and more preferably from about 5 to about 30 wt % or even from about 5 to about 25 wt %.

In addition, the green co-surfactant may be a cationic surfactant, particularly, ester-type and amide-type glycine based surfactants derived from a renewable raw material such as glycine betaine (from sugar beet) and European and/or tropical oils. Bipolar amphiphiles (bolaamphiphiles) combining a sugar polar head at one end and a cationic polar head at the other end may also be used.

The cleaning composition may optionally include one or more green linkers. The green linkers may be lipophilic or hydrophilic. Suitable lipophilic and hydrophilic linkers may include, but are not limited to, oleates (e.g., glycerol monooleate (GMO), glyceryl oleate, etc.), stearates (e.g., glycerol monostearate (GMS)), polysorbates (e.g., sorbitan monolaurate (SML)), alkanols, glucosides, esters, glycerin and mixtures thereof.

For example, the lipophilic linker may include one or more C12-18 alkanol. In one embodiment, the one or more alkanols may be selected from the group consisting of lauryl alcohol, cetyl alcohol, myristic alcohol, and mixtures thereof. The alkanols may be made from immediate predecessors that are obtainable from natural and renewable sources. In particular, lauryl alcohol may be made from fatty acids in coconut oils; cetyl alcohol may be made from spermaceti, a waxy substance obtained from sperm whale oil; and myristic alcohol may be made from myristic acid, which is found in palm oil, coconut oil, butter fat, and spermaceti.

Similarly, the hydrophilic linker may also be made from immediate predecessors that are obtainable from natural and renewable sources. Suitable hydrophilic linkers may include one or more alkyl glucoside such as hexyl glucoside. The hexyl glucoside used in the disclosed composition is commercially available (as "AG 6206") from Akzo Nobel, 525 W. Van Buren Street, Chicago, Ill. 60607-3823. The hydrophilic part of the hexyl glucoside, derived from glucose or dextrose, may be obtained from starch, most commonly from corn.

The green lipophilic and/or hydrophilic linkers may be used in the cleaning composition to synergistically improve the performance, such as soil removal and/or streak reduction, of the composition. As a result, relatively low levels of the green linkers are required. In one embodiment, the disclosed composition may include from 0.000001 to no more than 2 wt % green linker(s). In another embodiment, the green linker(s) may be included low levels of from 0.000001 to 1 wt % and still synergistically improve the performance of the composition.

Without wishing to be bound by any particular theory, linker molecules are added to the disclosed composition to enhance the interaction between the surfactant and oil (lipophilic linkers) or water (hydrophilic linkers) phases, where the lipophilic and hydrophilic linkers are combined to behave as a self-assembled surfactant at the oil/water interface to facilitate the formation of a stable micro-emulsion when the wipe is activated by water. Further, the efficiency of the self-assembly may be dependent on the ratio of the green surfactants and the green linkers, the total concentration of the surfactants and/or linkers, or both. In some embodiments, the self-assembly between hydrophilic and lipophilic linkers to facilitate the formation of micro-emulsions may require the presence of only a small amount of linkers, such as from about 0.01 wt % to about 0.1 wt %. In some embodiments, effective soil removal is achieved by compositions using linkers at a total concentration of 0.0012 wt % and 0.0024 wt %.

Again, although some preferred embodiments of this disclosure use only green linkers, other embodiments may include a combination of green and non-green linkers (e.g. synthetic linkers) or may even include only non-green linkers so long as the quantity of the non-green linkers does not significantly lower the Natural Index of the disclosed composition.

In some embodiments, the cleaning composition may optionally include one or more pH adjusting agents. Preferably, the pH adjusting agents used in the composition are derived from natural and renewable sources and thus do not negatively affect the ecological profile, i.e. Natural Index, of the composition.

Suitable pH adjusting agents may include bases such as sodium hydroxide (manufactured through electrolysis of salt solution), sodium carbonate (naturally occurring as mineral deposits), and sodium bicarbonate (naturally occurring in mineral natron). In addition, the green pH adjusting agents may include one or more organic acids derived from natural or renewable sources. For example, the organic acids may be citric acid (naturally occurring in fruits and vegetables), lactic acid (obtainable from fermentation of milk sugar, cornstarch, or potato), acetic acid (obtainable from fermentation of starch or fruit), etc. The use of lactic or citric acids may also have the benefit of soap scum and lime scale removal. Finally, the green pH adjusting agents may include one or more salts of the aforementioned organic acids, such as sodium citrate, sodium acetate, etc.

Of course, the type and concentration of the green pH adjusting agents suitable for use in the cleaning composition would be dependent on the desired pH of the composition and should be apparent to one of ordinary skill in the art without undue experimentation in light of this disclosure.

In some embodiments, e.g. glass cleaning wipes, the cleaning composition may optionally include one or more streak reduction agents. Preferably, the streak reduction agents used in the composition are derived from natural and renewable sources and thus do not negatively affect the ecological profile, i.e. Natural Index, of the composition.

Suitable green streak reduction agents may include salts of a green organic acid, such as salts of tartaric acid, etc. In one embodiment, the cleaning composition includes 0-0.001 wt % tartaric acid salt.

Of course, the type and concentration of the green streak reduction agents suitable for use in the cleaning composition would be dependent on the specific application of the composition and should be apparent to one of ordinary skill in the art without undue experimentation in light of this disclosure.

Disinfecting/Sanitizing Composition

As discussed above, the disinfecting/sanitizing composition includes at least one green disinfecting/sanitizing agent derived in from natural and renewable sources for providing antimicrobial or antibacterial benefit to a target surface. The green disinfecting/sanitizing agent may be selected from the group consisting of essential oil, colloidal silver, organic acids, and mixtures thereof.

Under EPA guidelines (http://www.epa.gov/oppad001/ad_info.htm), disinfectants are used on hard inanimate surfaces and objects to destroy or irreversibly inactivate infectious fungi and bacteria but not necessarily their spores; and sanitizers are used to reduce, but not necessarily eliminate, microorganisms from the inanimate environment to levels considered safe as determined by public health codes or regulations. In one embodiment, the disclosed composition may be used as a disinfectant. In another embodiment, the disclosed composition may be used as a sanitizer.

Essential oils for the disclosed composition may include botanic extracts that exhibit antimicrobial, antibacterial and/or antifungal activities. For example, suitable essential oils may include, but are not limited to, citronella oil, lemon eucalyptus oil, cinnamon oil, castor oil, rosemary oil, lemongrass oil, cedar oil, peppermint oil, clove oil, geranium oil, verbena oil, pennyroyal oil, lavender oil, pine oil, cajeput oil, basil oil, thyme oil, allspice oil, soybean oil, garlic oil, etc.

In one embodiment, the essential oil is selected from the group consisting of oregano oil, thyme oil, clove oil, rosemary oil, garlic oil, cinnamon oil, bay oil, lemongrass oil, Australian tea tree oil, citronella oil, geranium oil, avocado oil, and mixtures thereof. The essential oils may be included in the composition at a concentration of 0.001-2 wt %, more preferably at a concentration of 0.01-1 wt %. Of course, the type, strength, and concentration of the essential oils suitable for use in the disclosed composition would be apparent to one of ordinary skill in the art and therefore should not be considered as limiting the scope of this disclosure.

As another suitable green disinfecting/sanitizing agent, silver exhibits broad spectrum of activity and has been registered as a disinfectant with the EPA for over fifty years. In particular, colloidal silver is safe and effective in lower concentrations and is suitable for use in the disclosed composition. Colloidal silver may be electrolytically produced with a particle size of 0.001 to 0.01 micron. In one embodiment, the charged silver particles in the colloidal silver are complexed with citric acid, although other acids, such as acetic acid, may also be used to from the silver complex. To further improve the disinfecting/sanitizing performance of the composition, the colloidal silver may be stabilized and/or suspended, such as in a micro-emulsion, to prevent aggregation (or "falling out") of the silver particles.

In one embodiment, the colloidal silver used in the disclosed composition is available under Tinosan® SDC by Ciba Corporation, 4090 Premier Dr., High Point, N.C. 27265. The colloidal silver may be included in the composition at a concentration of 20-2000 ppm, more preferably at a concentration of 30-1000 ppm. However, it is to be understood that the type, strength, and concentration of the colloidal silver suitable for use in the disclosed composition would be apparent to one of ordinary skill in the art and therefore should not be considered as limiting the scope of this disclosure.

Organic acids suitable for used in the disinfecting/sanitizing composition may be derived in from natural and renewable sources. For example, the disinfecting/sanitizing composition may include one or more organic acids such as acetic acid, benzoic acid, citric acid, lactic acid, malic acid, sorbic acid, tartaric acid, etc. In one embodiment, the disinfecting/sanitizing composition includes a blend of colloidal silver and one or more organic acids to further enhance the antibacterial/antimicrobial performance of the composition.

The green disinfecting/sanitizing agent suitable for use in the cleaning composition may also include metals, metal salts, organic acids, and mixtures thereof. Suitable antimicrobial metals include, for example, Ag, Au, Pt, Pd, Ir, Cu, Sn, Sb, Pb, Bi, Zn and combinations thereof. Without wishing to be bound by any particular theory, the effectiveness of antimicrobial elemental metals is thought to be due to the formation of corresponding metal ions, such as through air oxidation. Likewise, salts of the antimicrobial metals may also be included in the cleaning composition. Upon dissolution, metal ions are released into the cleaning composition for providing antimicrobial benefits to the target surfaces. In one embodiment, the disinfecting/sanitizing composition includes a mixture of colloidal silver and copper or zinc (in either elemental or salt form).

Of course, the type, strength, and concentration of the green disinfecting/sanitizing agents suitable for use in the disinfecting/sanitizing composition would be apparent to one of ordinary skill in the art and therefore should not be considered as limiting the scope of this disclosure.

Fragrance Composition

The disclosed wipe may optionally include a fragrance composition containing green fragrance materials derived in from natural and renewable sources such as plants or crops. In addition, the composition may deliver the fragrances into the air in a controlled manner over a long period of time. The fragrance composition may function to mask one or more malodors on or by imparting a pleasant smell to the treated surface, or both. As is well known, a fragrance normally consists of a mixture of a number of fragrant materials, each of which has a particular fragrance. The number of fragrant materials in a fragrance is typically ten or more. The range of fragrant materials used may vary. The materials come from a variety of chemical classes, but in general are water-insoluble oils. In many instances, the molecular weight of a fragrance material is in excess of 150, but does not exceed 300.

The fragrance composition used in the disclosed wipe may be present in an amount that is sufficient to impart a pleasant smell to the air that can be perceived by a consumer. In the presence of a malodor, the natural fragrance may be present in an amount that masks at least a substantial portion of the malodor in the air. More preferably, the fragrance composition may be present in an amount that not only completely masks the malodors therein, but also delivers a pleasant smell to be perceived by a consumer.

The fragrance composition may be present in the disclosed wipe in an amount of from 0 to 0.5 wt %, more preferably from 0 to 0.2 wt % and most preferably from 0 to 0.1 wt %. The amount of the fragrance that is needed to mask the malodor(s) therein, and/or the amount of the fragrance to impart the pleasant smell to be perceived by the consumer will be apparent to one of ordinary skill in the art.

The fragrance composition according to this disclosure may comprise one or more fragrant materials or materials that provide chemically active vapors. In one embodiment, the fragrance can comprise and/or include volatile, fragrant compounds including, but not limited to natural botanic extracts, essences, fragrance oils, and so forth. As is known in the art, many essential oils and other natural plant derivatives contain large percentages of highly volatile scents. In this regard, numerous essential oils, essences, and scented concentrates are commonly available from companies in the fragrance and food businesses.

Exemplary oils and extracts include, but are not limited to, those derived from the following plants: almond, amyris, anise, armoise, bergamot, cabreuva, calendula, canaga, cedar, chamomile, coconut, eucalyptus, fennel, jasmine, juniper, lavender, lemon, orange, palm, peppermint, quassia, rosemary, thyme, and so forth.

Fragrances can also be made of organic compounds derived from floral materials and fruits. Examples of suitable organic compounds include, but are not limited to, dimyrcetol, phenylethyl alcohol and tetrahydromuguol, decyl aldehyde, undecyl aldehyde, undecylenic aldehyde, lauric aldehyde, amyl cinnamic aldehyde, ethylmethyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, parahydroxyphenolbutanone, 6-acetyl-1,1,3,4,4,6-hexamethyl tetrahydronaphthalene, alpha-methyl ionone, gamma-methyl ion-one, and amyl-cyclohexanone and mixtures thereof.

It is to be understood, of course, that the type, strength, and odor profile of the fragrance composition suitable for use in the disclosed wipe would be apparent to one of ordinary skill in the art and therefore should not be considered as limiting the scope of this disclosure.

Multi-Functional Wipe

As discussed above, the functional compositions may be impregnated in or coated on the substrate. In one embodiment, the substrate is a non-woven sheet with a plurality of distinct sections with which the functional compositions are releasably associated. For example, the substrate may include a first section for the cleaning composition, a second section for the disinfecting/sanitizing composition, and an optional third section for the optional fragrance composition. In one embodiment, the distinct sections are substantially parallel and separated strips located on one side of the substrate. In a refinement, one or more of the functional compositions may be impregnated in the distinct sections while other functional compositions are coated on the distinct sections. In another refinement, all functional composition may be either impregnated in or coated on the distinct sections. The distinct sections may also be located on difference sides of the substrate. In one embodiment, a side margin is provided on the sheet so that none of the distinct sections reaches any side edge of the sheet. In some other embodiment, the functional compositions are releasably associated with the substrate as randomly distributed or patterned patches although the functional compositions remain separated from one another.

To impregnate the functional compositions into the substrate, a functional composition may be formulated with water or one or more organic solvents into a liquid bath, in which the substrate (or distinct sections thereof) is soaked for a suitable amount of time. The substrate is then removed from the liquid bath and the solvent removed to yield a wipe with the functional composition impregnated therein.

To coat the functional compositions onto the substrate, a functional composition may be formulated with water or one or more organic solvents into a paste, which in turn is brushed or rolled onto the substrate (or distinct sections thereof) before the solvent removed to yield a wipe with the functional composition coated thereon.

Other techniques to incorporate the functional compositions into the substrate may also be used by one of ordinary skill in the art in view of this disclosure and should not be considered as limiting the scope of this disclosure. For example, the functional compositions may be added during the manufacturing process of the substrate, such as during extrusion and processing of the natural or synthetic fibers.

One feature of the disclosed wipe is that it is substantially free of water. High water content may decrease the amounts of the functional compositions that can be delivered to the target surface by each cleaning wipe. As a result, wipes with relatively high water contents may clean, disinfect/sanitize substantially less surface areas than the disclose wipe. Moreover, the functional compositions are separated from one another in the disclosed wipe before water-activation. Therefore, incompatibilities between the functional compositions should not significantly affect the multi-functional performances of the disclosed wipe.

The relatively low water content of the cleaning composition used in the disclosed wipe may also obviate the use of preservatives, which are otherwise necessary in cleaning compositions used in conventional wipes. Thus, In some embodiments, the disclosed wipe is essentially free of any preservatives. Further, the cleaning composition loaded on the disclose wipe is more concentrate, and thus may be loaded in smaller doses, than cleaning compositions used in conventional wet wipes. As a result, the disclose wipe weighs significantly less and is dry to the touch, which allows for more convenient and efficient storage, handling, and transportation.

Another feature of the cleaning composition used in the disclose wipe is its high Natural Index. As a result, the composition achieves improved performance without sacrificing the ecological profile thereof. For example, one or more of the functional compositions may have a high Natural Index of ranging from 85% to about 99%.

When the substrate of the disclose wipe is also made of green components such as natural or naturally derived fibers, the disclosed wipe may have a high Natural Index ranging from 85% to about 99%.

Method of Use

In a general embodiment, this disclosure relates to a method for cleaning and disinfecting/sanitizing a target surface, particularly household surfaces such as bathroom and shower surfaces, comprising the steps of: providing a multi-functional wipe in accordance with this disclosure; wetting the wipe with water to activate the wipe, i.e. to release the functional compositions from the substrate; and contacting the activated wipe with the target surface. Optionally, the method further includes the steps of rewetting the wipe and re-contacting the rewetted wipe with the target surface.

In one embodiment, the cleaning wipe is hand-applied onto the target surface. In another embodiment, the wipe is attached to the distal end of a cleaning device, such as a mop or sweeper. The wipe may be attached to the cleaning device prior to or after its activation. In a refinement, the cleaning device may include a water reservoir and a dispenser for spraying water directly onto the wipe when it is attached to the cleaning device.

As discussed above, the disclosed wipe is activated by water just prior to use. Water activation can be done by pouring water directly on the wipe or by quickly immersing the wipe into water. Alternatively, the target surface may be pre-wetted with water and the wipe may be activated by contacting the water on the target surface. The disclosed wipe may be activated multiple times. For example, the wipe may be first water-activated then used for cleaning and disinfecting/sanitizing, then reactivated as needed or until the cleaning and/or disinfecting/sanitizing compositions of the wipe substantially deplete.

One feature of the disclosed wipe is that the functional compositions may be rapidly and conveniently released from the substrate upon water-activation. To that end, warm or hot water is not necessary to activate the disclosed wipe, which further reduces water and energy consumption. Moreover, because water-activation occurs just prior to the cleaning process, tap water or even recycled water would be sufficient to activate the wipe. However, the disclosed wipe is certainly capable of being activated by hot or warm water, or by water of higher purities than tap or recycled water.

Typically, water activation is achieved by exposing the cleaning wipe directly to a water source readily available in the bathtub or shower enclosure area, such as a bathtub faucet or shower head. Water can also be sourced from other locations and transferred to the wipe or surface to be cleaned by means of, for example, syringes, garden hoses, spray bottles, containers, buckets, and the like.

The disclosed method is particularly adapted for remove soil, soap scum, lime scale, and other dirty substances from household surfaces. Moreover, the method may also provide additionally disinfecting/sanitizing and/or fragrance delivery benefits to the target surfaces without involving any additional steps or consuming any additional energy. It is to be understood that one of ordinary skill in the art would appreciate that despite the particular efficacy of the disclosed method and wipes for cleaning and disinfecting/sanitizing household surfaces, the same method and wipes can also be used to clean any other kind of inanimate surfaces, in particular hard surfaces in medical or commercial facilities.

While only certain embodiments have been set forth, alternatives and modifications will be apparent from the above description to those skilled in the art. These and other alternatives are considered equivalents and within the spirit and scope of this disclosure and the appended claims.

What is claimed is:

1. A cleaning wipe comprising:
   a substrate having at least a first section and a second section, the first section and the second section each being physically distinct regions of the substrate;
   a cleaning composition releasably associated with the first section, the cleaning composition comprising a green surfactant; and
   a disinfecting/sanitizing composition releasably associated with the second section, the disinfecting/sanitizing composition comprising a green disinfecting/sanitizing agent,
   wherein the first and second sections are positioned relative to each other to prevent contact between the cleaning composition and the disinfecting/sanitizing composition when the cleaning wipe is substantially free of water.

2. The wipe of claim 1, wherein the substrate is made of a fiber material selected from the group of natural fibers, naturally derived fibers, synthetic fibers, and blends thereof.

3. The wipe of claim 1, wherein the wipe has a Natural Index of at least 95%.

4. The wipe of claim 1, wherein the wipe is substantially free of water.

5. The wipe of claim 1, wherein the green surfactant is selected from the group consisting of green nonionic surfactants, green anionic surfactants, and mixtures thereof.

6. The wipe of claim 5, wherein the green surfactant is selected from the group consisting of alkylpolyglycosides, sodium coco sulfate, sodium lauryl sulfate, and mixtures thereof.

7. The wipe of claim 1, wherein the green disinfecting/sanitizing agent is selected from the group consisting of colloidal silver, organic acids, essential oils, and mixtures thereof.

8. The wipe of claim 7, wherein the organic acids are selected from the group consisting of citric acid, lactic acid, tartaric acid, malic acid, ferulic acid, and mixtures thereof.

9. The wipe of claim 1, further comprising a natural fragrance composition releasably associated with the substrate, the natural fragrance composition being separated from the cleaning composition and the disinfecting/sanitizing composition.

10. The wipe of claim 1, wherein the cleaning composition further comprises a green linker.

11. The wipe of claim 10, wherein the green linker is selected from the group consisting of hexadecanol, glyceryl monooleate, hexyl glucose, and mixtures thereof.

12. The wipe of claim 1, wherein at least one of the cleaning and disinfecting/sanitizing compositions is coated onto the substrate.

13. The wipe of claim 1, wherein at least one of the cleaning and disinfecting/sanitizing compositions is impregnated into the substrate.

14. A cleaning wipe comprising:
   a substrate having physically distinct first and second sections;
   a cleaning composition releasably associated with the first section, the cleaning composition comprising a green surfactant; and
   a disinfecting/sanitizing composition releasably associated with the second section that is separate from the first section, the disinfecting/sanitizing composition comprising a green disinfecting/sanitizing agent,
wherein the first and second sections are positioned relative to each other to prevent contact between the cleaning composition and the disinfecting/sanitizing composition when the cleaning wipe is substantially free of water, and
wherein the wipe has a Natural Index of at least 99%.

15. The wipe of claim 14, wherein the wipe is substantially free of water.

16. The wipe of claim 14, wherein the substrate further comprises a distinct third section and wherein the wipe further comprises a natural fragrance composition releasably associated with the third section.

17. The wipe of claim 14, wherein the cleaning composition further comprises a green linker selected from the group consisting of hexadecanol, glyceryl monooleate, hexyl glucose, and mixtures thereof.

* * * * *